(12) United States Patent
Aust et al.

(10) Patent No.: US 6,365,137 B1
(45) Date of Patent: Apr. 2, 2002

(54) SKIN WHITENING AGENTS

(75) Inventors: Duncan T. Aust, Ridge; James M. Wilmott, Shoreham, both of NY (US)

(73) Assignee: Collaborative Laboratories, Inc., Stony Brook, NY (US)

( * ) Notice: Subject to any disclaimer, the term of this patent is extended or adjusted under 35 U.S.C. 154(b) by 0 days.

(21) Appl. No.: 09/544,650

(22) Filed: Apr. 6, 2000

Related U.S. Application Data (60) Provisional application No. 60/127,931, filed on Apr. 6, 1999.

(51) Int. Cl.[7] .......................... A61K 7/135; A61K 7/00
(52) U.S. Cl. ..................... 424/62; 424/401; 514/844
(58) Field of Search ................... 424/62, 401; 514/844

(56) References Cited

U.S. PATENT DOCUMENTS 3,812,251 A    5/1974  Mima et al. ............... 424/148
5,733,535 A  * 3/1998  Hollingshead et al. ........ 424/65

FOREIGN PATENT DOCUMENTS

WO    WO 99/07362    2/1999

* cited by examiner

*Primary Examiner*—Thurman K. Page
*Assistant Examiner*—Rachel M. Bennett
(74) *Attorney, Agent, or Firm*—Darby & Darby

(57) ABSTRACT

Disclosed are stable compositions which are effective as skin whitening agents, comprising alpha, beta or gamma substituted mono-, di or polyhydroxy or polycarboxy carboxylic acids; mono-, di, tri or polyhydroxy alkyl compound; and effective amounts of an inhibitor of tyrosinase and a pigmentation reversing reagent. Also disclosed are methods of forming stable compositions of the type described above.

22 Claims, 11 Drawing Sheets

SKIN WHITENING AGENTS

This application claims benefit of 60/127,931 filed Apr. 6, 1999.

FIELD OF THE INVENTION

This invention is directed to the field of compositions for use as skin whitening agents.

BACKGROUND OF THE INVENTION

Exposure to the sun over time can induce many biochemical reactions in the skin. For example, exposure can lead to sunburn and tanning, which are immediate and well recognized. Other consequences of exposure to the sun are more subtle and accumulate over time. Often melanocytes can accumulate and the action of the enzyme tyrosinase is increased. These changes can result in the development of age spots and create an uneven, mottled skin tone. Unfortunately, many of the commercially available products in today's market are either only marginally effective, or contain active agents that are unstable and lose their potency when incorporated into a final formula.

The ability to modify the expression of pigment content in the skin, to promote an even-looking skin tone and a more youthful appearance, is highly desired in today's society. Many people desire to modify their skin tone, to reduce aging spots, melasma, etc., or for purely cosmetic reasons. In fact, in the Far East, a lighter skin tone is desirable and is associated with higher socio economic status.

Hyper-pigmentation in the skin is caused by the over expression or accumulation of melanin in the skin. As a result, the pathway involved in melanin production has been the target for many inhibitors so as to reduce the levels produced. One of the principal enzymes involved in the melanin pathway is tyrosinase, and there are many commonly used inhibitors of this enzyme. Unfortunately, there are many stability issues associated with the majority of these active agents when incorporated into aqueous systems. One of the most potent tyrosinase inhibitors, kojic acid, is prone to oxidation leading to breakdown and severe color changes in certain formulations. Ascorbic acid has also been used for its whitening properties and like kojic acid is prone to oxidation in aqueous systems. Indeed ascorbic acid is highly unstable in aqueous systems and degrades much more rapidly than most of the other whitening actives.

U.S. Pat. No. 3,812,251 to Mima et al., describes an aqueous composition containing ascorbic acid phosphate stabilized by the addition of boric acids and water-soluble salts.

Further, PCT Patent Application WO 99/07362 discloses a process for stabilizing levogyre ascorbic acid (LAA) by adding at least one compound linked to the LAA by hydrogen bridges. An LAA emulsion containing a least one hydrogen bonded compound is produced. However, WO '362 describes compositions which are limited to use in solutions and serums. WO '363 does not describe or suggest compositions which can be incorporated into cosmetic emulsions and similar formulations.

It would be desirable to those skilled in the art to realize a way of formulating a composition which can be effectively used as a topically applied skin whitening agent. In particular, identifying a composition that has improved stability and efficacy relative to those described in the prior art would be of significant commercial interest.

Applicants have now discovered stable compositions comprising tyrosinase inhibitors, which are useful in topically applied cosmetic and pharmaceutical formulations.

OBJECTS OF THE INVENTION

It is an object of the present invention to provide a composition of matter which will enhance or improve the appearance of skin by evening skin tone.

It is another object of the present invention to provide a composition of matter which includes a polyhydroxy or polycarboxy carboxylic acid, such as lactic acid; a polyhydroxy alkyl compound (such as glycerin); and two or more active agents which are useful as tyrosinase inhibitors and/or pigmentation reversing agents.

SUMMARY OF THE INVENTION

The invention is directed to stable, homogeneous compositions which are effective as skin whitening agents. The compositions of the invention comprise
  (a) at least one alpha, beta or gamma substituted mono-, di or polyhydroxy or polycarboxy carboxylic acid;
  (b) at least one mono-, di, tri or polyhydroxy alkyl compound; and one or more of
  (c) an effective amount of an inhibitor of tyrosinase; and
  (d) an effective amount of a pigmentation reversing reagent.

The invention may comprise one or more of any of the tyrosinase inhibitors or pigmentation reversing agents known in the art, and in particular may include one or more of the tyrosinase inhibitors pigmentation reversing agents further described herein.

In particular embodiments, the mono-, di or polyhydroxy or polycarboxy carboxylic acid is an alpha or beta hydroxy acid, such as lactic, glycolic, malic or citric acid. In particular embodiments, the mono-, di, tri or polyhydroxy alkyl compound is glycerin, sorbitol, mannitol, polyol, propylene glycol, ethylene glycol, butylene glycol, hexylene glycol and mixtures thereof.

The invention is also directed in part to methods of forming the stable, non-irritating compositions of the invention. Methods of the invention include coupling a hydroxy acid, a hydroxy alkyl compound, a tyrosinase inhibitor, and a pigmentation reversing agent, with a carboxylic acid activating agent to generate a homogeneous composition.

In another embodiment, methods of the invention include forming a stable, non-irritating composition having skin whitening properties, comprising the steps of forming a mixture of glycerin, a tyrosinase inhibitor, a pigmentation reversing agent, and lactic acid; heating the mixture and mixing until the mixture is clear and homogeneous.

The invention is also directed to methods of lightening the skin color of a human, or methods of evening the skin tone of a human, comprising contacting the skin of a human with a composition of the invention.

DETAILED DESCRIPTION OF THE INVENTION

All patents, applications, test methods and publications referenced in this specification are hereby incorporated by reference in their entirety. In case of conflict, the present description, including definitions, will prevail.

The present invention is directed in part to compositions which is useful as a skin whitening agent that does not have the stability problems associated with whitening agents currently available. Specifically, the invention is directed in part to compositions comprising stable, homogeneous compositions comprising a) at least one alpha, beta or gamma substituted mono-, di or polyhydroxy or polycarboxy carboxylic acid;

(b) at least one mono-, di, tri or polyhydroxy alkyl compound;

(c) an effective amount of an inhibitor of tyrosinase; and (d) an effective amount of a pigmentation reversing reagent.

Suitable tyrosinase inhibiting agents include, but are not limited to, kojic acid, glycyrrhetinic acid, glycyrrhizinic acid, arbutin, vinyl guaicol, tyrosine, tyrosine derivatives, deoxyphenylalanine, dopaquinone, mimosine, benzhydroxamic acid, 2,3-dithiopropanol, tropolone, azelaic acid, or mixtures thereof. Preferred is kojic acid.

Suitable pigment reversing agents include ascorbic acid, isoascorbic acid, dehydroascorbic acid, ascorbic acid phosphate, mono- or dialkyl derivatives of ascorbic acid or ascorbic acid phosphate, mono or dialkyl derivatives of ascorbic acid or ascorbic acid phosphate, or mixtures thereof. Ascorbic acid is preferred.

Suitable mono-, di, or polyhydroxy or polycarboxy polycarboxylic acids include, but are not limited to kojic acid, ascorbic acid, caffeic acid, salicylic acid, methyllactic acid, glucoronic acid, lactic acid, glycolic acid, pyruvic acid, 2-hydroxybutanoic acid, 2-hydroxypentanoic acid, 2-hydrohexanoic acid, mandelic acid, benzylic acid, phenyllactic acid, gluconic acid, galacturonic acid, mannuronic acid, glucunolactone, glucoronolactone, mannuronolactonre, alluronic acid, altruronic acid, guluronic acid, iduronic acid, taluronic acid, galactonic acid, mannonic acid, gulonic acid, idonic acid, galactonic acid, talonic acid, citric acid, aleuritic acid, tartronic acid, tartaric acid, malic acid, fumaric acid, benzene-1,4-bis (3-methylene-10-camphorsulfonic) acid, and mixtures thereof.

Preferred are alpha or beta hydroxy acids, more preferably the alpha hydroxy acids, such as lactic, glycolic, malic or citric acid. DL lactic acid or L lactic acid is most preferred.

Suitable mono-, di, tri or polyhydroxy alkyl compounds include, but are not limited to, glycerin, sorbitol, mannitol, polyol, propylene glycol, ethylene glycol, butylene glycol, hexylene glycol and mixtures thereof. Preferred compounds include glycerin, sorbitol, mannitol, polyol, propylene glycol, butylene glycol and mixtures thereof. Glycerin is most preferred.

Esters of the above mentioned active agents are believed to be helpful in formulating cosmetic products with greater color stability, chemical stability, and lower potential for skin irritation than formulation with the free acid active agents. In addition, the solubility properties of the acids may be sufficiently modified upon esterification that they may be more easily formulated into hydrophobic products without precipitation.

The present inventors have discovered that the proven tyrosinase inhibitor kojic acid can be combined with ascorbic acid to produce a truly efficacious skin whitening agent. The reaction used to produce the compositions of this invention results in a complex ascorbyl, kojyl and lactyl derivative ensuring efficacy and stability. This composition complex produced by the process of this invention inhibits the production and appearance of the pigment. Further, the composition stimulates migration of cells to the surface through gentle exfoliation, thereby reducing the concentration of melanin in the epidermis.

The mechanism of formation of the composition of the invention is only partially understood. However, it is believed that the compounds in the composition form a complex (containing hydrogen bonding or similar interactions) and also covalent bonding, thereby increasing stability.

In a preferred embodiment of this invention, the composition contains D,L lactic acid, glycerin, ascorbic acid and kojic acid. In a more preferred embodiment, the composition of this invention contains D,L-lactic acid in an amount ranging from about 5 to 95% by weight of the composition, glycerin in an amount ranging from about 1 to 95% by weight of the composition, ascorbic acid in an amount ranging from about 0.001 to 30% by weight of the composition, and kojic acid in an amount ranging from about 0.001 to 50% by weight of the composition. In more preferred embodiment, the composition comprises about 40–50 wgt % D,L-lactic acid; about 40–50 wgt % glycerin; about 1–5 wgt % ascorbic acid; and about 2–10 wgt % kojic acid.

In another preferred embodiment, the composition of this invention contains lactic acid-DL in an amount of about 50.0 wgt %, glycerin in an amount about 47 wgt %, ascorbic acid in an amount about 1 wgt % and kojic acid in an amount about 2.0 wgt %.

The compositions of this invention were found to be a non-irritant in dermal irritation testing at concentrations up to 5% in systems with a pH of 4.0, and preferred embodiments were found to be a non-irritants at concentrations up to 1%. Moreover, the compositions described herein displayed minimal ocular irritation at a 1% level making the composition considerably less irritating then lactic acid when tested under similar conditions.

Methods of forming the compounds of the invention include processes comprising heating and mixing a hydroxy acid, a polyhydroxy alkyl compound, a tyrosinase inhibitor, and a pigmentation reversing agent, to generate a homogeneous composition. In alternative methods, the process includes coupling a hydroxy acid, a hydroxy alkyl compound, a tyrosinase inhibitor, and a pigmentation reversing agent, with a carboxylic acid activating agent to generate a homogeneous composition. Additional methods of the invention include forming a mixture of glycerin, a tyrosinase inhibitor, a pigmentation reversing agent, and lactic acid; heating the mixture to greater than 70° C. and mixing until clear and homogeneous.

When present, carboxylic acid activating agents assist in the formation of coupling (covalent bonding) between or among the hydroxy or carboxy moieties of the compounds in the composition. Suitable carboxylic acid activating agents include carbodiimide and carbodiimidazole derivatives, such as alkyl carbodiime derivative. An exemplary carboxylic acid activating agent is 1,3-dimethylaminopropyl-3-ethyl carbodiimide.

In order to further illustrate the present invention, the experiments described in the following examples were carried out. It should be understood that the invention is not limited to the specific examples or the details described therein. The results obtained from the experiments described in the examples are shown in the accompanying figures and tables.

EXEMPLARY EMBODIMENTS OF THE INVENTION

Figure 1:
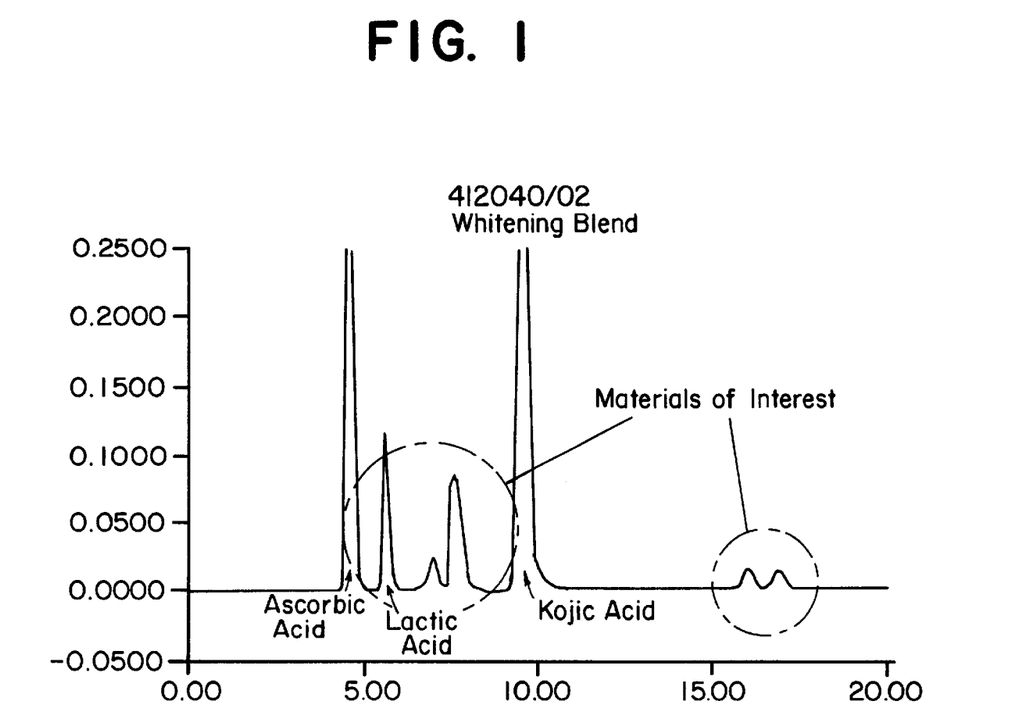
FIG. 1 shows an HPLC fingerprint of a mixture of ascorbic acid, kojic acid, glycerin and lactic acid.
Figure 2:
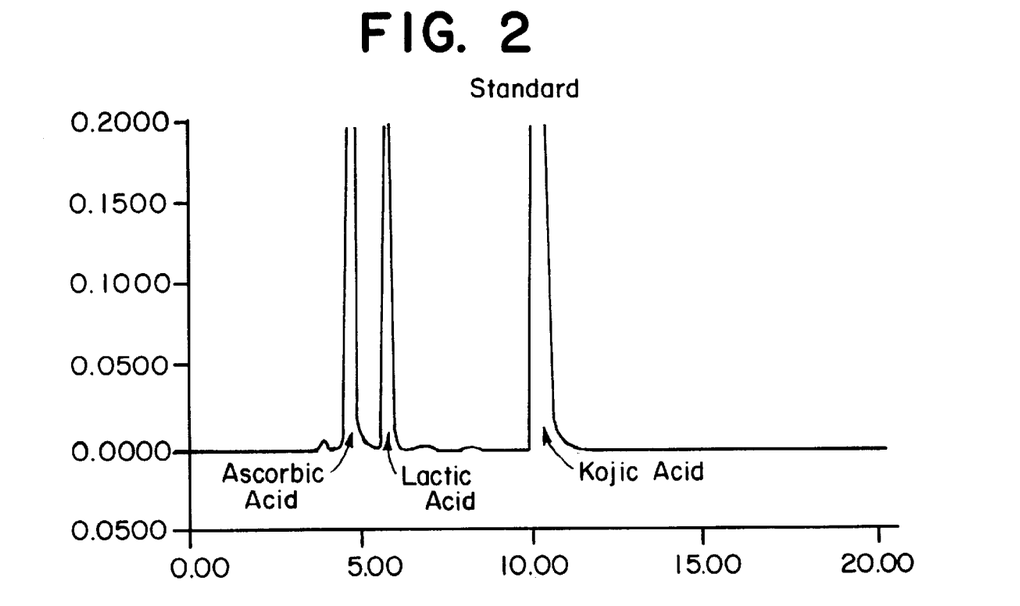
FIG. 2 shows an HLPC fingerprint of a mixture of ascorbic acid, kojic acid, glycerin and lactic acid which has been heated after mixture to 70–80° C. to initiate a reaction.

FIG. 1 depicts the HPLC fingerprint of a mixture of ascorbic acid, kojic acid, glycerin and lactic acid. FIG. 2 depicts the HPLC fingerprint of a mixture of ascorbic acid, kojic acid, glycerin and lactic acid which has been heated after mixture to 70–80° C. to initiate a reaction.

Example 1

In a first beaker, approximately 150 g lactic acid was heated to approximately 70° C. and mixed until clear. In a second beaker, 138.18 g glycerin was mixed with 2.97 g ascorbic acid and 6.0 g kojic acid. The composition was heated to approximately 75° C. and mixed until clear. The contents of the two beakers were combined and mixed until uniform. The resulting composition was tested for its ability to inhibit tyrosinase activity and for its whitening potential.

Example 2

To determine the formation of stable esters, lactic acid was mixed with glycerin, ascorbic acid, or kojic acid individually and heated to 110° C. with mild agitation for a desired time period. It is believed that lactic acid forms esters with itself, resulting in dimers, glycerin, ascorbic acid, or kojic acid via Fischer esterification when subjected to moderately elevated temperatures in an anhydrous environment. Progress of the reaction that occurred was monitored by reversed phase HPLC with photodiode array detection.

The chemicals used in Example 2 were: lactic acid (90%, Fluka); glycerin (99.5%, Aldrich); ascorbic acid (99+%, EM Industries); kojic acid (Sigma); de-ionized water; methanol; acetonitrile (both HPLC grade, EM Sciences); and phosphoric acid (85%).

A programmable hotplate/stirrer (PMC 720 series) was used. The HPLC system consisted of a Waters (Milford, Mass.) model 600e quaternary gradient controller and pump equipped with a column heater, a Waters model 717 autosampler, and a Waters model 996 photodiode array detector. The columns used to perform the separation were 250 mm×4.6 mm Inertsila $C_8$ and ODS3 ($C_{18}$), Metachem technologies, Inc. (Torrance, Calif.), which were plumbed in series. The data acquisition software was Waters Millennium, version 3.05.01.

Three reaction mixtures were set in separate 250 ml beakers at 110±5° C. for a desired period of time (2–3.5 hrs) and stirred at 300 rpm. Reaction mixtures (1) to (3) were prepared as follows:

1) lactic acid (70.1 g) and glycerin (30.0 g);
2) lactic acid (99.0 g) and ascorbic acid (5.0 g); and
3) lactic acid (100.4 g) and kojic acid (5.0 g). At various time points the reaction mixtures were sampled (~1 ml) for HPLC analysis. Reactions of ascorbic acid with glycerin were also monitored to determine the formation of glycerin ester.

All samples were diluted with neat HPLC grade methanol to a concentration of approximately 5–8 mg/ml, filtered through 0.45 mm nylon syringe filters into 1 ml glass HPLC vials, and analyzed via HPLC. Column details and solvent gradients are shown below:

Metachem Inertsil $C_8$ 250×4.6 and Metachem Inertsil ODS3 250×4.6 columns were prepared in series.

The results of the testing are depicted below in Table 1.

TABLE 1

| | | Solvent Gradient Table Percent Solvent | | | | |
|---|---|---|---|---|---|---|
| Time | Flow | % A | % B | % C | % D | Curve |
| 0.00 | 1.00 | 100.0 | 0.0 | 0.0 | 0.0 | |
| 10.00 | 1.00 | 100.00 | 0.0 | 0.0 | 0.0 | 6 (linear) |
| 30.00 | 1.00 | 65.00 | 0.0 | 35.0 | 0.0 | 6 (linear) |
| 60.00 | 1.00 | 100.00 | 0.0 | 0.0 | 0.0 | 11 (none) |

Solvents A to D are Identified Below.
  Solvent A 0.085% Aqueous phosphoric acid
  Solvent B Methanol
  Solvent C Acetonitrile
  Solvent D Empty
  All samples were examined at 208 nm analytical wavelengths. In addition, the lactic acid-ascorbic acid preparation was examined at 243 mm, and the lactic acid-kojic acid preparation was examined at 267 nm.

Figure 3A:
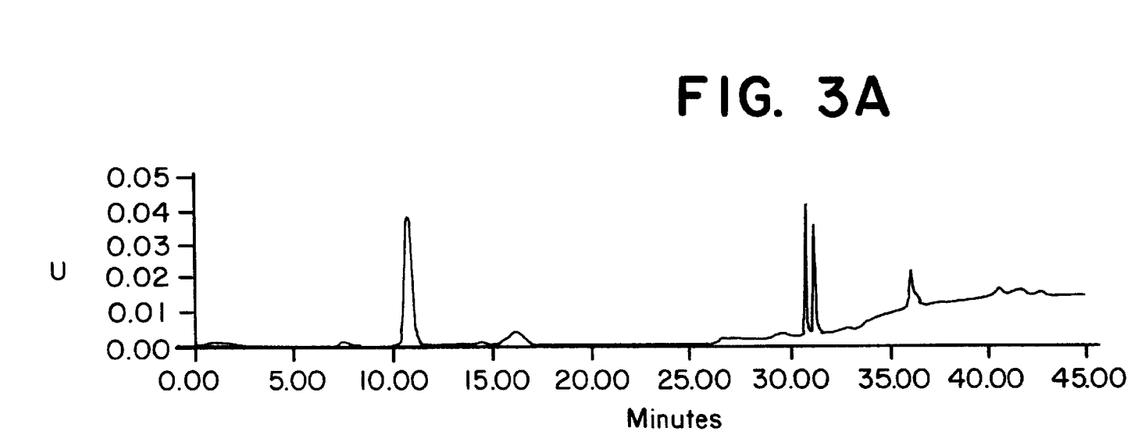
FIGS. 3(A) to 3(C) are HPLC chromatograms of a reaction mixture of glycerin and lactic acid.
Figure 3B:
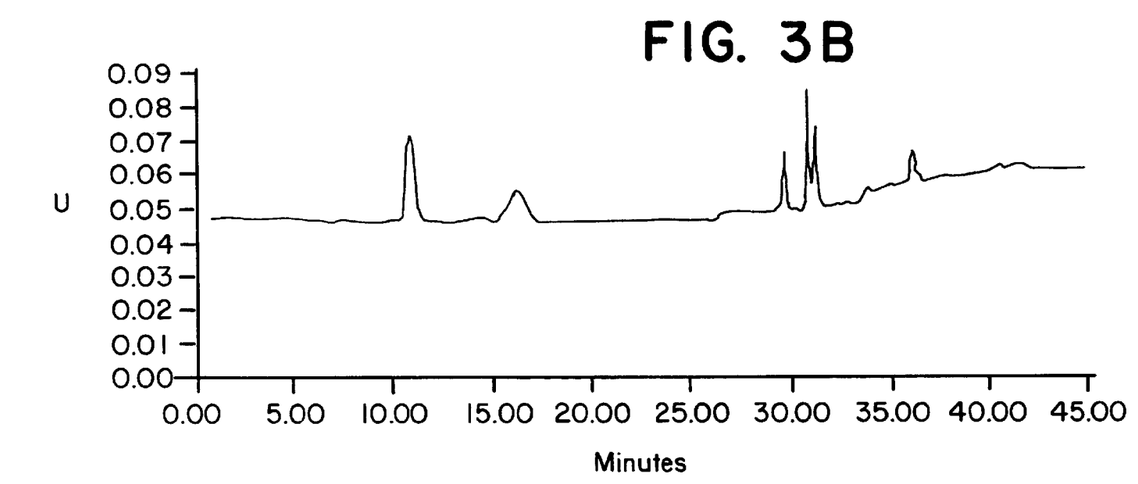
Figure 3C:
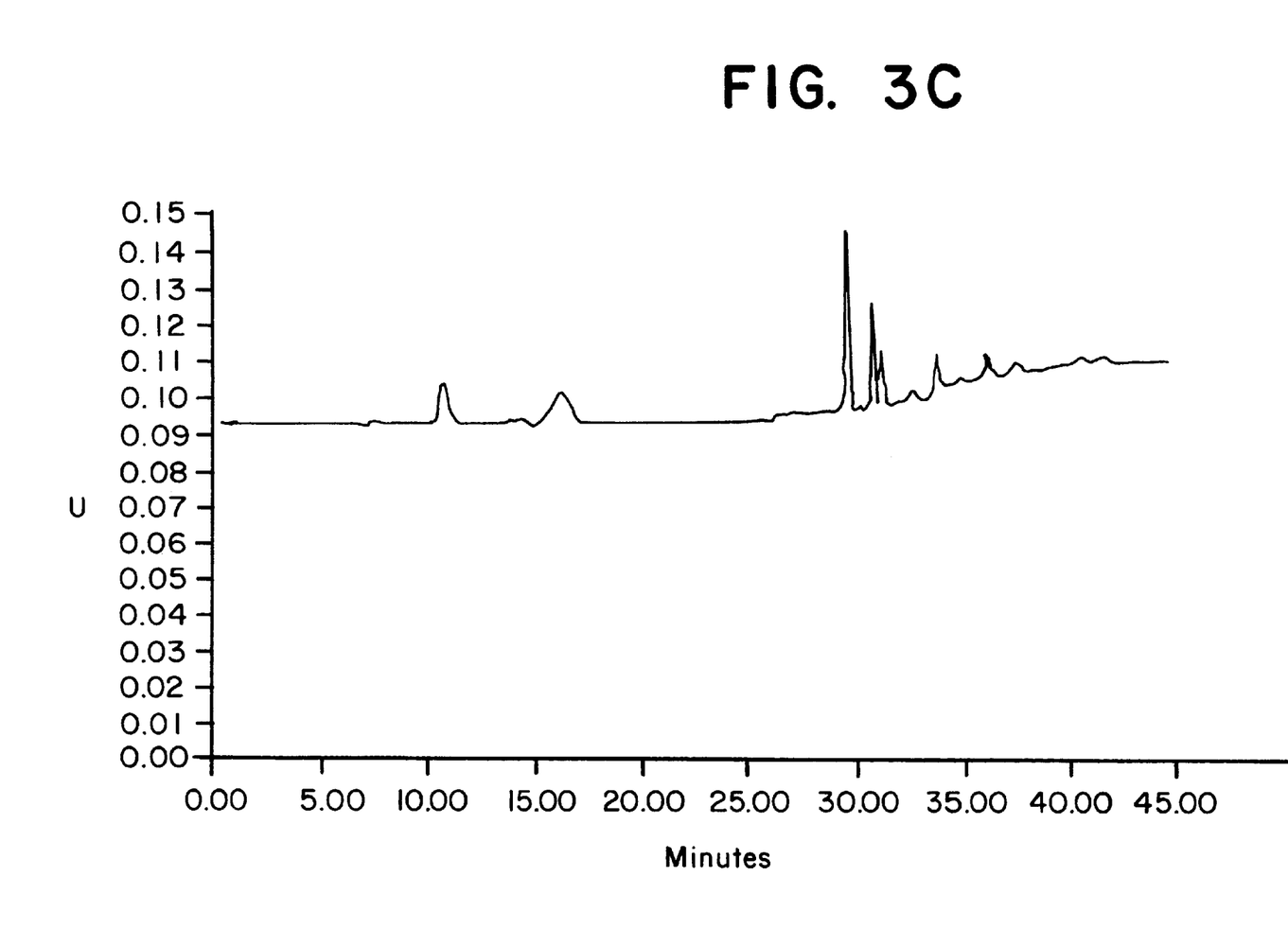
Figure 4A:
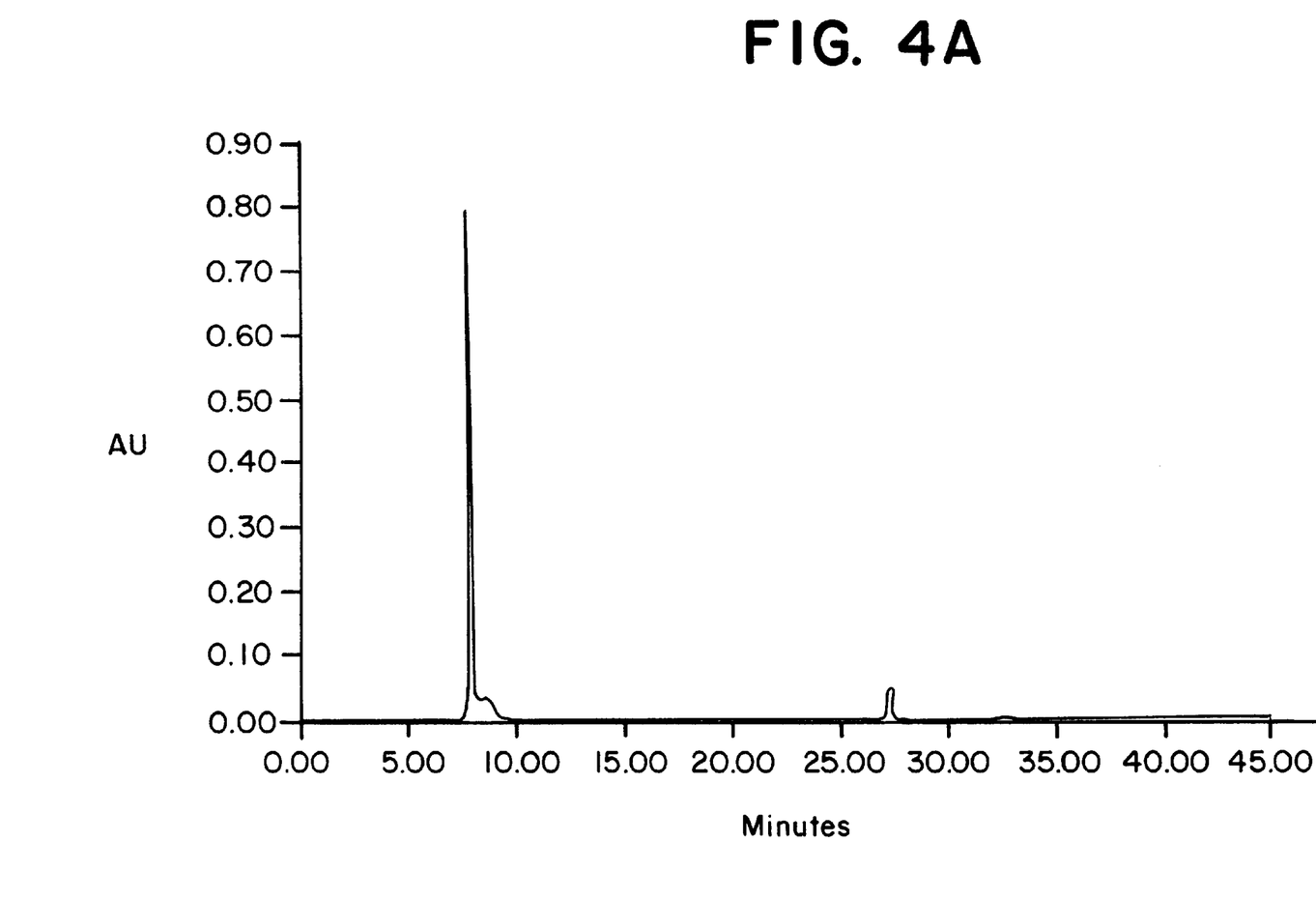
FIGS. 4(A) to 4(C) are HPLC chromatograms of a reaction mixture of ascorbic acid and lactic acid.
Figure 4B:
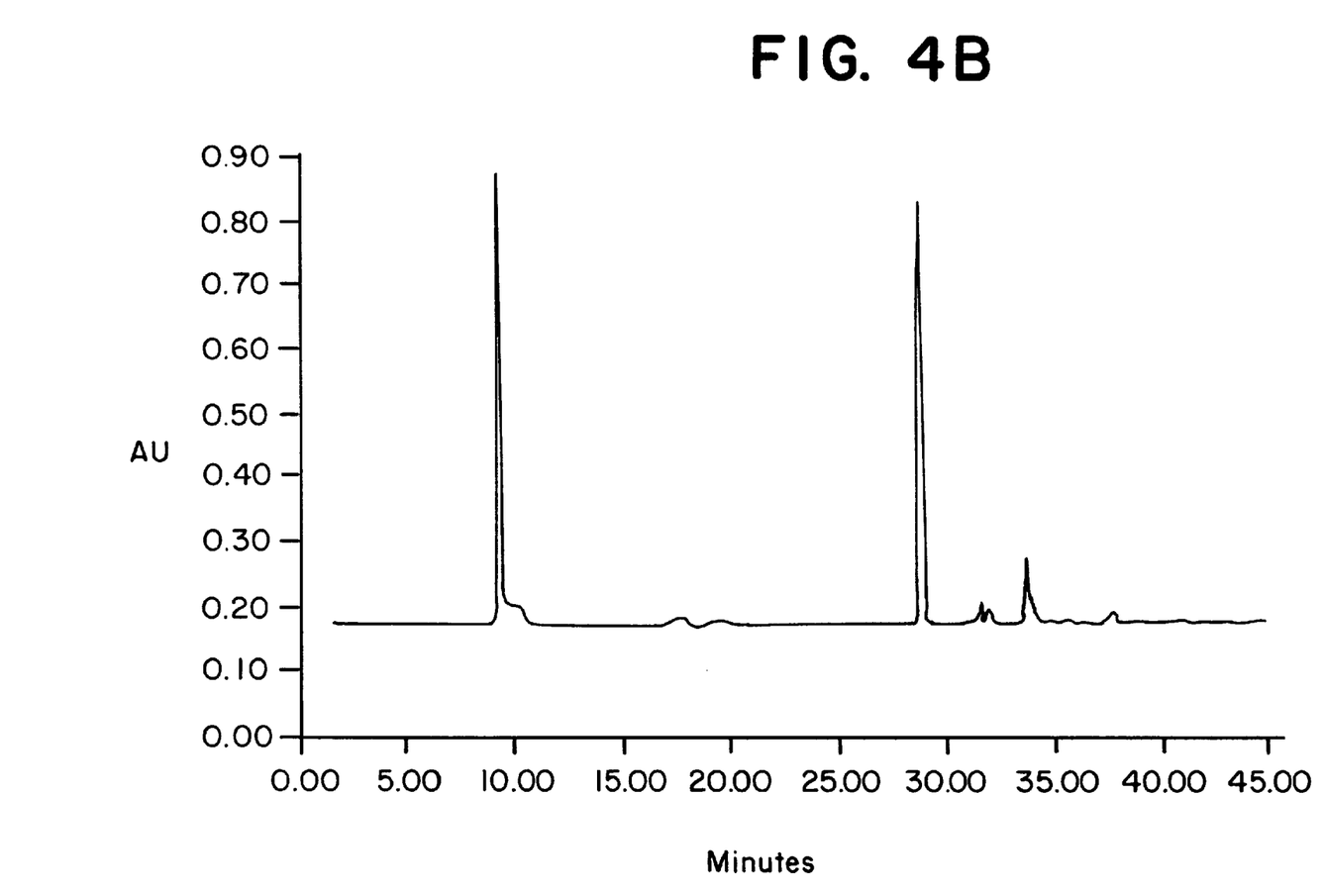
Figure 4C:
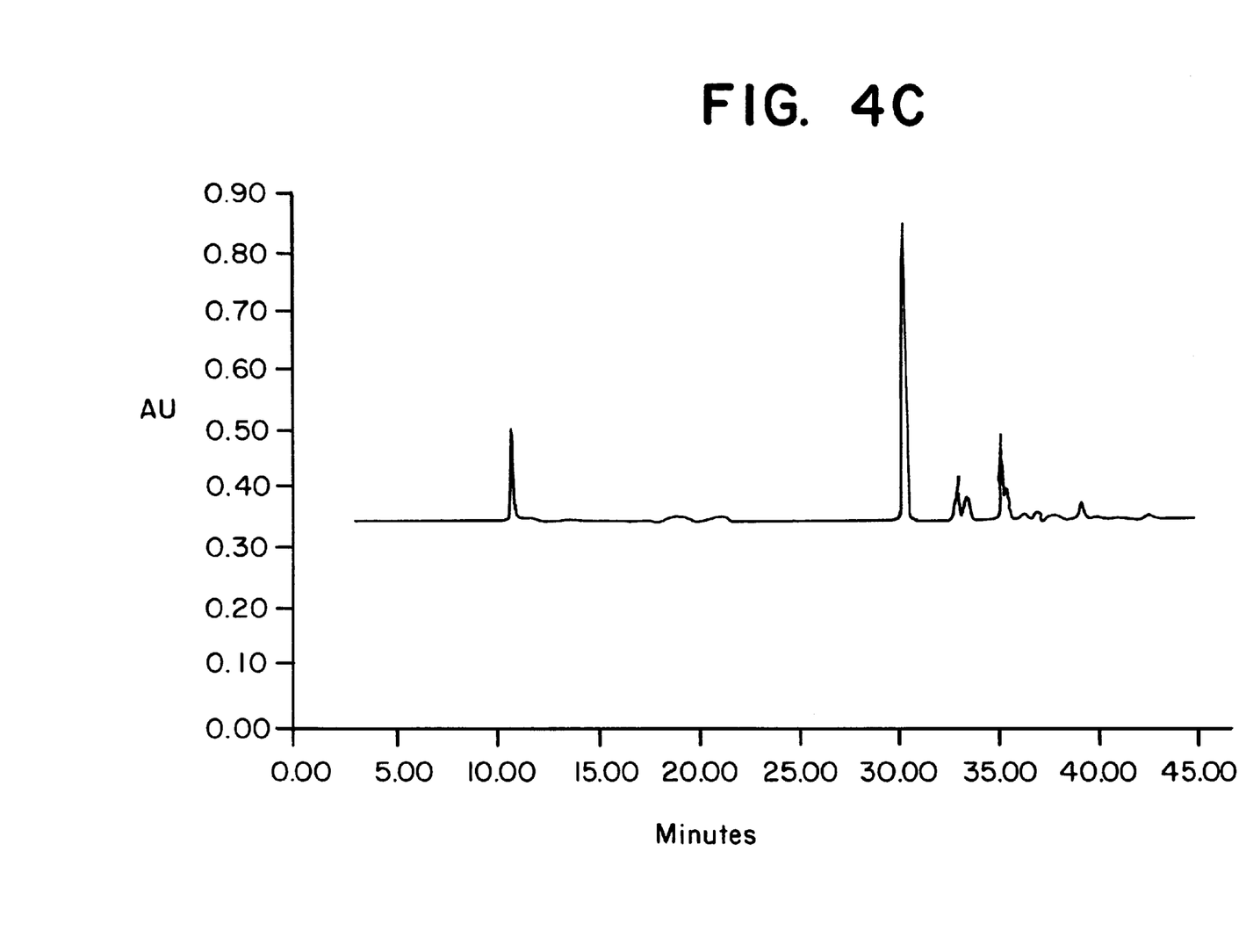
Figure 5A:
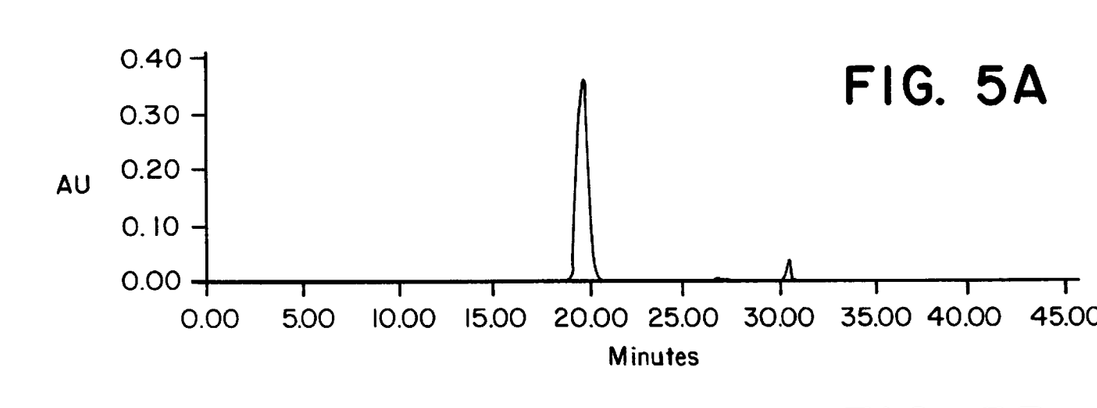
FIGS. 5(A) to 5(C) are HPLC chromatograms of a reaction mixture of kojic acid and lactic acid.
Figure 5B:
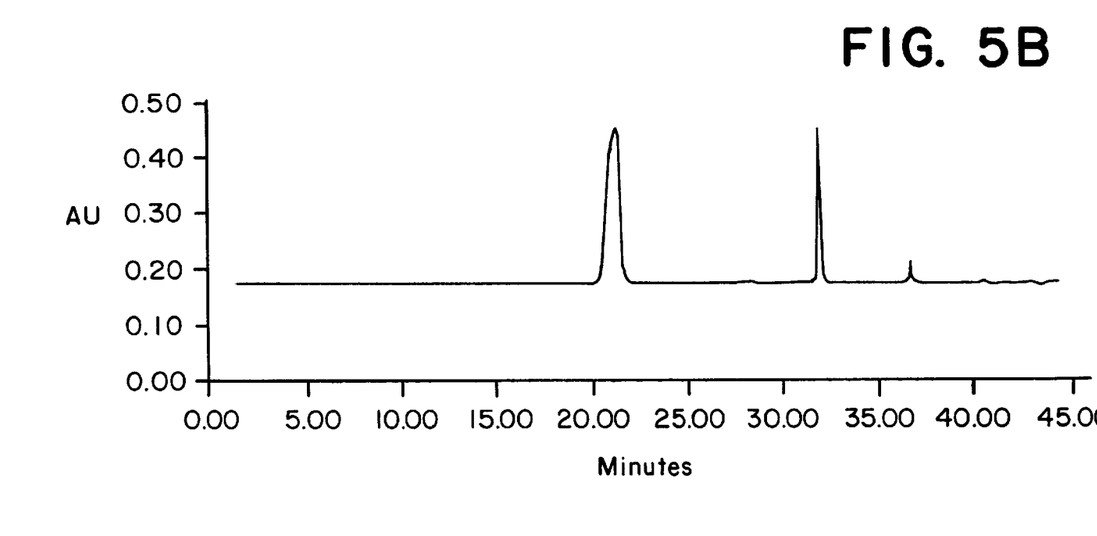
Figure 5C:
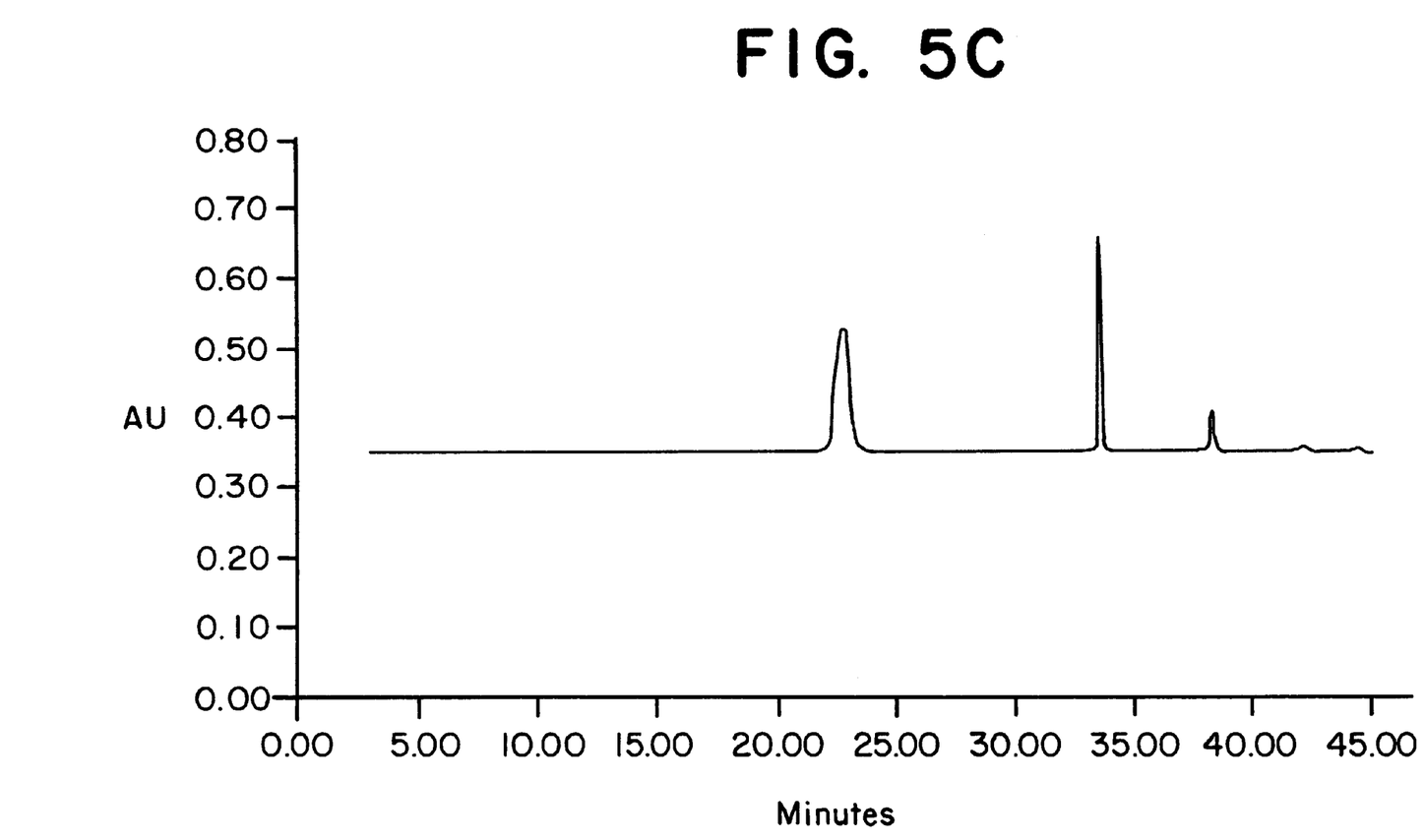

All three preparations showed evidence of lactate ester formation when analyzed by HPLC. In all cases, the concentrations of the starting materials whose presence was detectable by HPLC decreased over time. At the same time, new peaks with UV spectra very similar to those of the starting materials (with distinctive chromophores) became apparent and increased over time. It is also suspected that lactic acid formed dimers with itself and possibly pyruvic acid, because the same two peaks at 30.7 and 31.1 minutes are seen in all chromatograms taken at 208 nm. FIGS. 3 through 5 show overlaid chromatograms of the three sets of reaction mixtures indicating that a coupling reaction occurred between lactic acid and glycerin, ascorbic acid, and kojic acid. The newly synthesized compounds are hydrolyzed in the presence of sodium hydroxide, as an ester would be.

FIGS. 3(A) to 3(C) show HPLC chromatograms of reaction mixtures of glycerin and lactic acid at 7 min (A), 58 min (B), and 214 min (C) into reaction. Peak #1 indicates lactic acid. Peaks #2 indicate suspected dimers of lactic acid (in HPLC trace A) or glyceryl lactates as the reaction progressed with time.

FIGS. 4(A)–4(C) show an HPLC chromatograms of reaction mixtures of ascorbic acid and lactic acid at 23 min (A), 88 min (B), and 128 min (C) into reaction. Peak #1 indicates ascorbic acid. Peaks #2 indicate suspected ascorbyl lactates.

FIGS. 5(A) to 5(C) show HPLC chromatograms of reaction mix of kojic acid and lactic acid at 13 min (A), 70 min (B), and 131 min (C) into reaction. Peak #1 indicates kojic acid, peaks #2 indicate suspected kojyl lactates.

The data indicates that glycerin, ascorbic acid, and kojic acid form stable esters with lactic acid. The data also indicates that glycerin did not react with ascorbic acid to form glyceryl ester, probably due to the fact that ascorbic acid does not have carboxylic group. Similarly, kojic acid, which also does not have a carboxylic group, is not expected to react with glycerin to form an ester.

Example 3

In Vivo Study of the Whitening Agent

Five female volunteers aged 25–30 with mild to moderate uneven skin tone and brown spots were selected by a dermatologist and were enrolled in a 4 week clinical study. A formulation containing 5% of Example 1. The formulation contained the following:

(A) 84.95% Deionized water
  0.25% NatroSol™ hydroxyethyl cellulose
  0.20% Keltrol™ xanthan gum
(B) 2.00% Halosol™ (1% solution of sodium hyaluronate)
  1.00% Phytosol Bearberry glycerin extract
  1.00% MicromerolTm glycerin and apple extract (Collaborative Labs.)
  0.50% TEA (triethanolamine)
  1.00% Licorice
  1.00% Germaben II preservative (Sutton)
(C) 1.00% BV OSE (Vitamin C derivative)
  0.10% Vitamin E Acetate, USP
(D) 2.00% Sepigel 305 acylamide copolymers (SEPPIC)
(E) Example 1

The formulation was applied twice daily to each volunteer on a selected skin area. Photographs of the skin were taken before the first application and at the end of the study. Images were digitized and quantitative information was obtained on the number and intensity of brown spots.

Figure 6A:
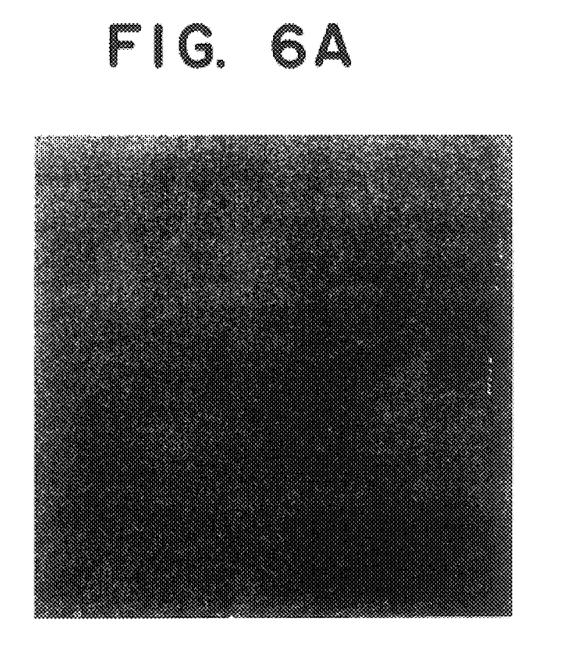
FIGS. 6(A) and 6(B) depict photographs of the skin of a person before and after a four week clinical treatment with a skin whitening agent composition of the invention.
Figure 6B:
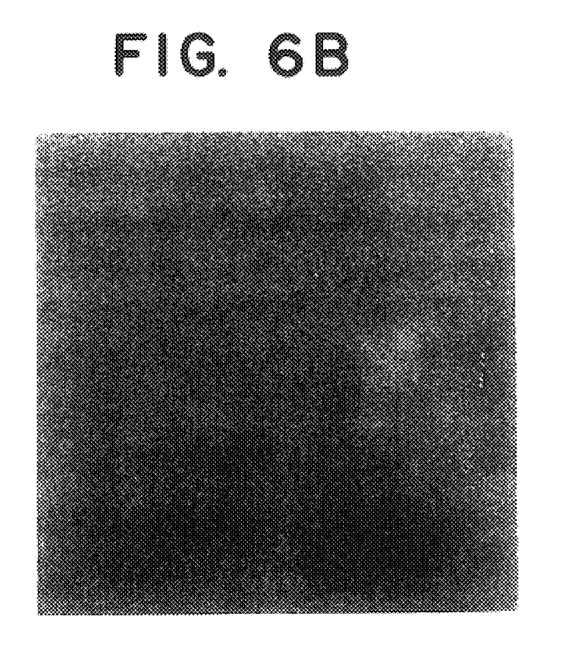

As shown in FIGS. 6A and 6B, a typical area of volunteer's skin before (left side) and after end of 4 week study (right side) of effectiveness of the whitening agent indicates that number and intensity of the brown spots on the skin being reduced upon treatment.

Figure 7:
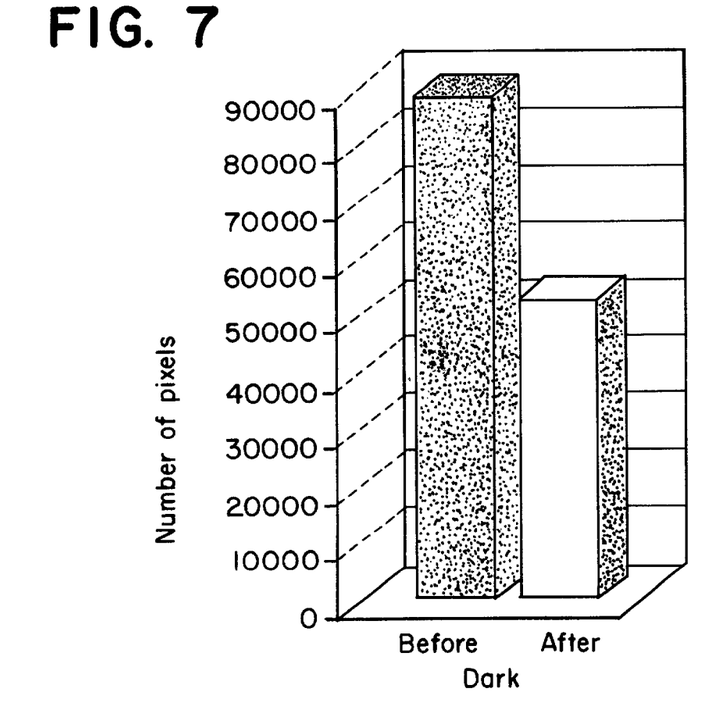
FIG. 7 depicts a quantitized analysis of digitized skin images from FIGS. 6(A) and 6(B), indicating the number of brown pixels on the skin both before and after the study.

FIG. 7 contains a quantitative analysis of digitized skin images (from FIGS. 6A and 6B) indicating number of brown pixels before after the study.

Figure 8:
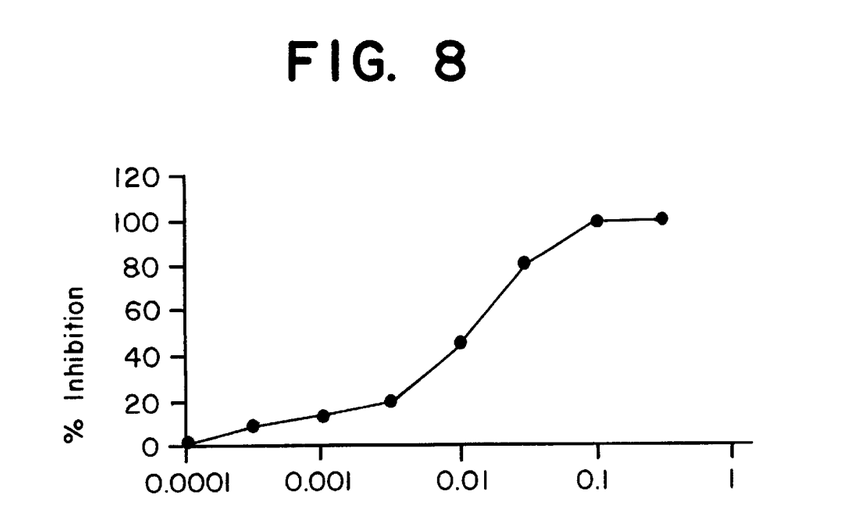
FIG. 8 depicts the results of in vitro tyrosinase activity.
Figure 9:
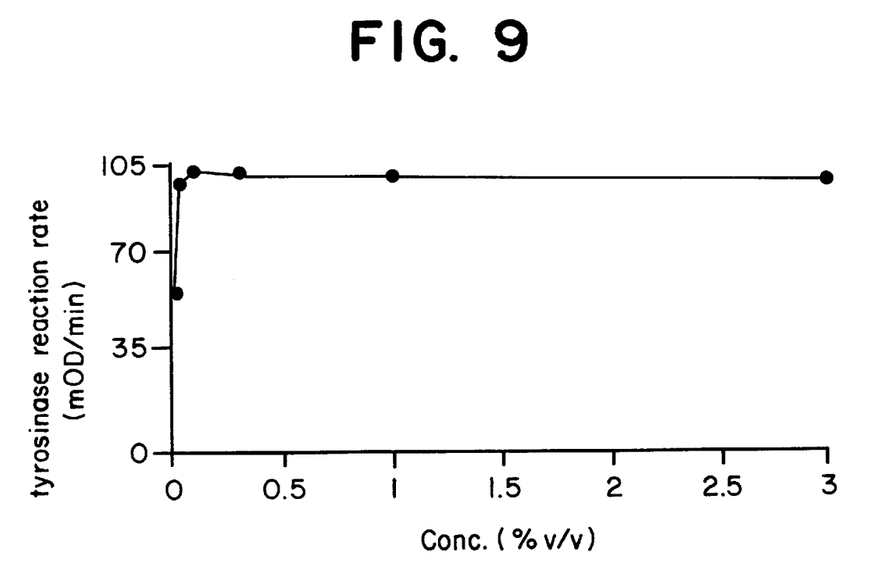
FIG. 9 shows the results of the tyrosinase inhibition assay for the ascorbyl glyceryl lactate composition of Example 1.

FIG. 8 shows in vitro tyrosinase activity studies which demonstrate greater than 95% inhibition of tyrosinase activity at as low as 0.03% w/w.

Example 4

Tyrosinase Inhibition Assay (Test for Whitening Activity)

Tyrosinase activity is determined in reaction mixtures containing 275 mM tyrosine, 30 units/ml of mushroom tyrosinase (EC 1.14.18.1), 75 mM sodium phosphate (pH 7.5), and test sample at the indicated concentrations. The reaction is conducted at room temperature and is monitored by measuring the increase in OD405 as melanin pigment is produced.

Materials:

The following materials were used in the tyrosinase assay:—Tyrosine T8909, Tyrosinase (mushroom) T7755, Hydroquinone H9003, and Sodium Phosphate S7907 and S8282 were obtained from Sigma. Optical density readings were determined using a Dynatech MR5000 spectrophotometer.

Methods:

Tyrosinase activity was determined by measuring the rate of change of optical density at 490 nm as tyrosine was converted into dopachrome. (Tyrosinase catalyzes the conversion of tyrosine into DOPA quinone, which spontaneously converts into dopachrome.) The rate of tyrosinase activity in the presence of various concentrations of test sample was measured at room temperature in a reaction mixture containing 50 mM sodium phosphate (pH 6.75), 275 $\mu$M tyrosine and 25U/ml mushroom tyrosinase (wherein U refers to the units of enzyme activity. Readings were made at one minute intervals for ten minutes and the reaction rate was calculated by linear regression. Each concentration was run in triplicate. Inhibition of tyrosinase activity was expressed as a percentage of the activity measured for the untreated control mixture (no test sample). An $EC_{50}$ (the concentration of test sample that inhibits 50% of tyrosinase activity) was calculated. Hydroquinone was tested in each assay as a positive control for inhibition of tyrosinase activity.

The results of the tyrosinase inhibition assay of the composition of Example 1 are depicted below in Table 1.

TABLE 1

Tyrosinase Inhibition Assay Results

| Sample | | mod/min | | |
|---|---|---|---|---|
| ID | Concentration | mean | se | % inhibition |
| Ascorbyl | 3 | 0.11 | 0.04 | 99.0 |
| Glyceryl | 1 | 0.14 | 0.00 | 98.7 |
| Lactate | 0.3 | 0.15 | 0.12 | 98.6 |
| (% v/v) | 0.1 | 0.02 | 0.03 | 99.8 |
| | 0.03 | 0.50 | 0.15 | 95.4 |
| | 0.01 | 4.78 | 0.41 | 56.0 |
| Control | 0 | 10.86 | 0.23 | — |
| Hydroquinone | 20 | 0.85 | 0.01 | 92.2 |
| (M) | 10.5 | 2.63 | 0.13 | 75.8 |
| | 2.5 | 5.92 | 0.03 | 45.5 |
| | 1.25 | 7.95 | 0.23 | 26.7 |
| | | 9.54 | 0.40 | 12.2 |

Example 5

Cell-Based Whitening/Tanning Assay

Materials

The following materials were used in the melanocyte pigmentation assay. Cloudman S91 cells (36-1-38C8–16) were obtained from American Type Culture Collection. Dulbecco's Modified Eagle's Medium ("DMEM"; 11885–076), heat-inactivated horse serum (26050-088), heat-inactivated fetal bovine serum (10082-147) and 5000units/ml penicillin/50$\mu$g/ml streptomycin (15070-063) were obtained from Gibco BRL. Phosphate-buffered saline (PBS; 1000–3), dimethyl sulfoxide (D2650), hydroquinone (H9003), α-melanocyte stimulating hormone (M4135), trichloroacetic acid (T9159) and sodium hydroxide (S8045) were obtained from Sigma. Optical densities were determined using a Dynatech MR5000 spectrophotometer.

Methods

The melanocyte pigmentation assay measures a test sample's ability to inhibit pigmentation. Cloudman S91 melanocytes were seeded into multiwell plates in medium (Dulbecco's Modified Eagle's Medium containing 15% heat-inactivated horse serum, 2.5% heat-inactivated fetal bovine serum, 50 units/ml penicillin and 50$\mu$g/ml streptomycin) containing 10nM -melanocyte stimulating hormone and varying concentrations of the test sample or 30$\mu$M hydroquinone (the positive control for inhibition of pigmentation). After a 5-day treatment period with each condition tested in triplicate wells, the cells were harvested by washing with PBS and adding 5% trichloroacetic acid to each well. After a 15 minute incubation the acid was aspirated and replaced with 200μl/well of 10% dimethyl sulfoxide/1N sodium hydroxide. The plates were sealed and incubated at 65° C. for 30 minutes. 200μl of each digestion mixture was then transferred to a well of a 96-well microtiter plate and optical densities were read at 405 nm.

Inhibition of pigmentation is expressed as the percentage decrease in optical density compared to that for untreated cells (no test sample or hydroquinone). An $EC_{50}$ (the concentration of test sample that inhibits 50% of pigmentation) was calculated for each sample.

TABLE 3

Cell Based Whitening Assay Results

| Sample ID | Concentration | mean SE | % Stimulation (+)/ Inhibition (−) |
|---|---|---|---|
| Ascorbyl Glyceryl Lactate % v/v | 3 | 0.113 0.35 | 91.1 |
| | 1 | 0.035 0.001 | 97.2 |
| | 0.3 | 0.484 0.002 | 67.1 |
| | 0.1 | 0.773 0.013 | 38.8 |
| | 0.03 | 1.062 0.007 | 16.0 |
| | 0.01 | 1.230 0.009 | 2.7 |
| Hydroquinone | 30 | 0.801 0.008 | 36.6 |
| GM + 10-8M MSH | — | 1.264 0.062 | — |

Figure 10:
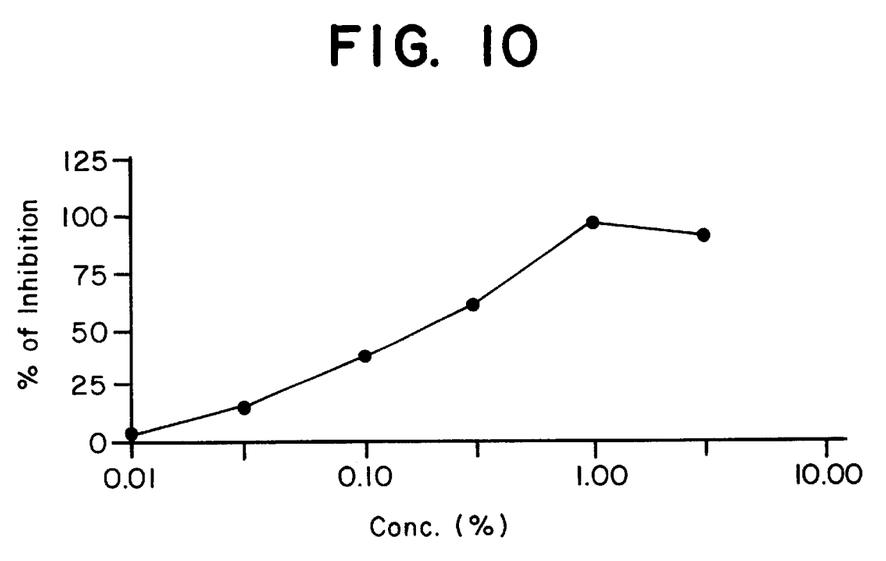
FIG. 10 shows the results of the cell-based whitening/tanning assays for an ascorbyl glyceryl lactate of Example 1.

Using a melanocyte cell based assay, the results in FIG. 10 show that compositions of this invention have a whitening potential between 0.03–0.3%.

What is claimed is:

1. A stable composition which is effective as a skin whitening agent, said composition comprising:
   (a) at least one alpha, beta or gamma substituted mono-, di or polyhydroxy or polycarboxy carboxylic acid;
   (b) at least one mono-, di, tri or polyhydroxy alkyl compound;
   (c) an effective amount of an inhibitor of tyrosinase;
   (d) an effective amount of a pigmentation reversing reagent; and
   (e) a carboxylic acid activating agent selected from the group consisting of a carbodiimide or a carbodiimidazole derivative.

2. The composition of claim 1, wherein said polyhydroxy or polycarboxy carboxylic acid is selected from the group consisting of kojic acid, ascorbic acid, caffeic acid, salicylic acid, methyllactic acid, glucuronic acid, lactic acid, glycolic acid, pyruvic acid, 2-hydroxybutanoic acid, 2-hydroxypentanoic acid, 2-hydrohexanoic acid, mandelic acid, benzylic acid, phenyllactic acid, gluconic acid, galacturonic acid, mannuronic acid, glucunolactone, glucuronolactone, mannuronolactone, alluronic acid, altruronic acid, guluronic acid, iduronic acid, taluronic acid, galactonic acid, mannonic acid, gulonic acid, idonic acid, galactonic acid, talonic acid, citric acid, aleuritic acid, tartronic acid, tartaric acid, malic acid, fumaric acid, benzene-1,4-bis (3-methylene-10-camphorsulfonic) acid, and mixtures thereof.

3. The composition of claim 1, wherein said acid is either an alpha or beta hydroxy acid.

4. The composition of claim 3, wherein the acid is an alpha hydroxy acid.

5. The composition of claim 4, wherein the alpha hydroxy acid is lactic, glycolic, malic or citric acid.

6. The composition of claim 5, wherein the alpha hydroxy acid is D, L-lactic acid or L lactic acid.

7. The composition of claim 1, wherein the mono-, di, tri or polyhydroxy alkyl compound is selected from the group consisting of glycerin, sorbitol, mannitol, polyol, propylene glycol, ethylene glycol, butylene glycol, hexylene glycol and mixtures thereof.

8. The composition of claim 7, wherein mono-, di, tri or polyhydroxy alkyl compound is selected from the group consisting of glycerin, sorbitol, mannitol, polyol, propylene glycol, butylene glycol and mixtures thereof.

9. The composition of claim 7, wherein the polyhydroxy compound is glycerin.

10. The composition of claim 1, wherein the inhibitor of tyrosinase is selected from the group consisting of kojic acid, glycyrrhetinic acid, glycyrrhizinic acid, arbutin, vinyl guaicol, tyrosine, tyrosine derivatives, deoxyphenylalanine, dopaquinone, mimosine, benzhydroxamic acid, 2,3-dithiopropanol, tropolone, azelaic acid, or mixtures thereof.

11. The composition of claim 10 wherein the inhibitor of tyrosinase is kojic acid.

12. The composition of claim 1, wherein the pigment reversing agent is selected from the group consisting of ascorbic acid, isoascorbic acid, dehydroascorbic acid, ascorbic acid phosphate, mono- or dialkyl derivatives of ascorbic acid or ascorbic acid phosphate, or mixtures thereof.

13. The composition of claim 12, wherein the pigment reversing agent is ascorbic acid.

14. The composition of claim 1, comprising about 5% to about 95% by weight D, L-lactic acid; about 1% to about 95% by weight glycerin; about 0.001% to about 30% by weight ascorbic acid; and about 0.001% to about 50% by weight kojic acid.

15. The composition of claim 14, comprising about 40–50 % by weight D, L-lactic acid; about 40–50 % by weight glycerin; about 1–5 % by weight ascorbic acid; and about 2–10% by weight kojic acid.

16. The composition of claim 5, wherein said glycerin, ascorbic acid and kojic acid form esters with lactic acid.

17. The composition of claim 1 which is a non- irritant in dermal irritation testing at up to 5% in systems with a pH of 4.0.

18. A cosmetic product comprising the composition of claim 14.

19. A method of forming a stable, non-irritating composition having skin whitening properties, said method comprising coupling a hydroxy acid, a hydroxy alkyl compound, a tyrosinase inhibitor, and a pigmentation reversing agent, with a carboxylic acid activating agent comprising a carbodiimide or a carbodiimidazole derivative to generate a homogeneous composition.

20. A method of lightening the skin color of a human, said method comprising contacting the skin of a human with a composition of claim 1.

21. The method of claim 19 wherein the carboxylic acid activating agent is 1,3-dimethylaminopropyl-3-ethyl carbodiimide.

22. The composition of claim 1, wherein the carboxylic acid activating agent is 1,3-dimethylaminopropyl-3-ethyl carbodiimide.

* * * * *